(12) United States Patent
Friedman et al.

(10) Patent No.: US 10,548,688 B2
(45) Date of Patent: Feb. 4, 2020

(54) DEVICE AND METHOD FOR HEATING DENTAL COMPOSITE MATERIALS

(71) Applicant: AdDent, Inc., Danbury, CT (US)

(72) Inventors: Joshua Friedman, Danbury, CT (US); Alex Lippay, Kent, CT (US)

(73) Assignee: AdDent, Inc., Danbury, CT (US)

( * ) Notice: Subject to any disclaimer, the term of this patent is extended or adjusted under 35 U.S.C. 154(b) by 0 days.

(21) Appl. No.: 16/204,055

(22) Filed: Nov. 29, 2018

(65) Prior Publication Data

US 2019/0090980 A1 Mar. 28, 2019

Related U.S. Application Data

(63) Continuation-in-part of application No. 15/645,615, filed on Jul. 10, 2017, now Pat. No. 10,172,690.

(51) Int. Cl.
*A61C 5/62* (2017.01)
*A61C 5/55* (2017.01)
*A61C 5/66* (2017.01)

(52) U.S. Cl.
CPC ............ *A61C 5/62* (2017.02); *A61C 5/55* (2017.02); *A61C 5/66* (2017.02)

(58) Field of Classification Search
None
See application file for complete search history.

(56) References Cited

U.S. PATENT DOCUMENTS

| | | |
|---|---|---|
| 4,582,488 A | 4/1986 | Newman |
| 4,704,088 A | 11/1987 | Newman |
| 4,734,560 A * | 3/1988 | Bowen ............... A01M 1/2077 261/DIG. 89 |
| 5,462,206 A | 10/1995 | Kwasie |
| 5,881,924 A | 3/1999 | Bokros |
| 5,988,445 A | 11/1999 | Massena |
| 6,142,207 A | 11/2000 | Richardot |
| 6,209,752 B1 | 4/2001 | Mitchell et al. |

(Continued)

OTHER PUBLICATIONS

Mamunya et al. "PTC Effect and Structure of Polymer Composites Based on Polyethylene/Polyoxymethylene Blend Filled With Dispersed Iron," Department of Physics, National Technical University of Athens, Athens, Greece, 2007 (pp. 34-42).

*Primary Examiner* — Yogesh P Patel
(74) *Attorney, Agent, or Firm* — Pearl Cohen Zedek Latzer Baratz LLP

(57) ABSTRACT

A combination heater assembly made of positive temperature coefficient (PTC) material such as barium titanate ceramic that may be self-regulating. A dental compule may be generally cylindrical, or another shape, and may hold a dental (e.g. composite) material. The compule may be made from conventional plastic or thermally conductive plastic. A compule may also be made from electrically conductive plastic that is self-heating when an electric current is passed through the compule. A compule may be generally cylindrical and include an electrically conductive polymer that may exhibit PTC characteristics while generating heat when electric current is applied to the polymer through two flat contact areas each disposed along one portion of the generally cylindrical compule, an orifice or opening positioned at one end of the compule, an inner chamber; and extrudable dental material held within the inner chamber.

14 Claims, 15 Drawing Sheets

(56) References Cited

U.S. PATENT DOCUMENTS

| | | | | |
|---|---|---|---|---|
| 6,312,254 B1* | 11/2001 | Friedman | ............... | A61C 5/62 |
| | | | | 433/32 |
| 6,494,715 B1 | 12/2002 | Riebl et al. | | |
| 6,527,143 B1 | 3/2003 | Schomacker | | |
| 6,616,448 B2 | 9/2003 | Friedman | | |
| 7,097,452 B2 | 8/2006 | Friedman | | |
| 7,520,409 B2 | 4/2009 | Smith et al. | | |
| 9,867,442 B1* | 1/2018 | Kose | ............... | A45D 2/48 |
| 2003/0165793 A1* | 9/2003 | Yobel | ............... | A61C 5/62 |
| | | | | 433/90 |
| 2004/0088817 A1 | 5/2004 | Cochran et al. | | |
| 2005/0170313 A1 | 8/2005 | Pitz et al. | | |
| 2005/0186532 A1 | 8/2005 | Friedman | | |
| 2006/0063126 A1 | 3/2006 | Aloise et al. | | |
| 2008/0039575 A1 | 2/2008 | Mercx | | |
| 2008/0187883 A1 | 8/2008 | Lee et al. | | |
| 2009/0069756 A1 | 3/2009 | Larsen | | |
| 2009/0298010 A1* | 12/2009 | Broyles | ............... | A61C 9/0026 |
| | | | | 433/90 |
| 2010/0237098 A1 | 9/2010 | Kaufman | | |
| 2011/0129794 A1 | 6/2011 | Pauser | | |
| 2011/0143305 A1 | 6/2011 | Wagner et al. | | |
| 2011/0266563 A1* | 11/2011 | Peter | ............... | B82Y 10/00 |
| | | | | 257/88 |
| 2011/0297891 A1 | 12/2011 | Mercx et al. | | |
| 2012/0088207 A1 | 4/2012 | Berkovich et al. | | |
| 2015/0022999 A1* | 1/2015 | Yu | ............... | F21K 9/90 |
| | | | | 362/84 |
| 2015/0079538 A1 | 3/2015 | Li et al. | | |
| 2016/0270876 A1 | 9/2016 | Fisher et al. | | |
| 2016/0278835 A1* | 9/2016 | Liang | ............... | A61B 17/8819 |
| 2017/0119970 A1 | 5/2017 | Bammer et al. | | |
| 2017/0128158 A1 | 5/2017 | Jung et al. | | |

\* cited by examiner

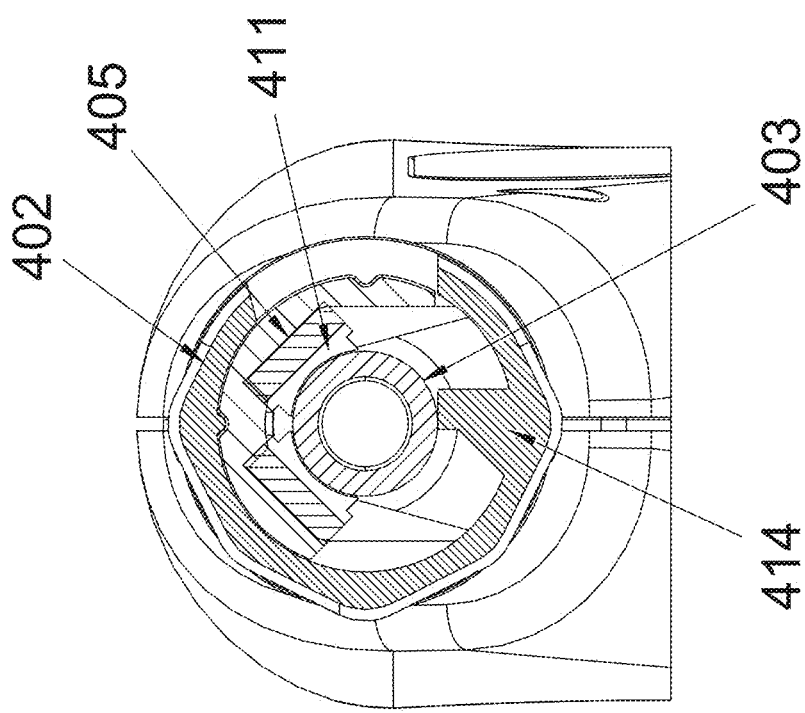
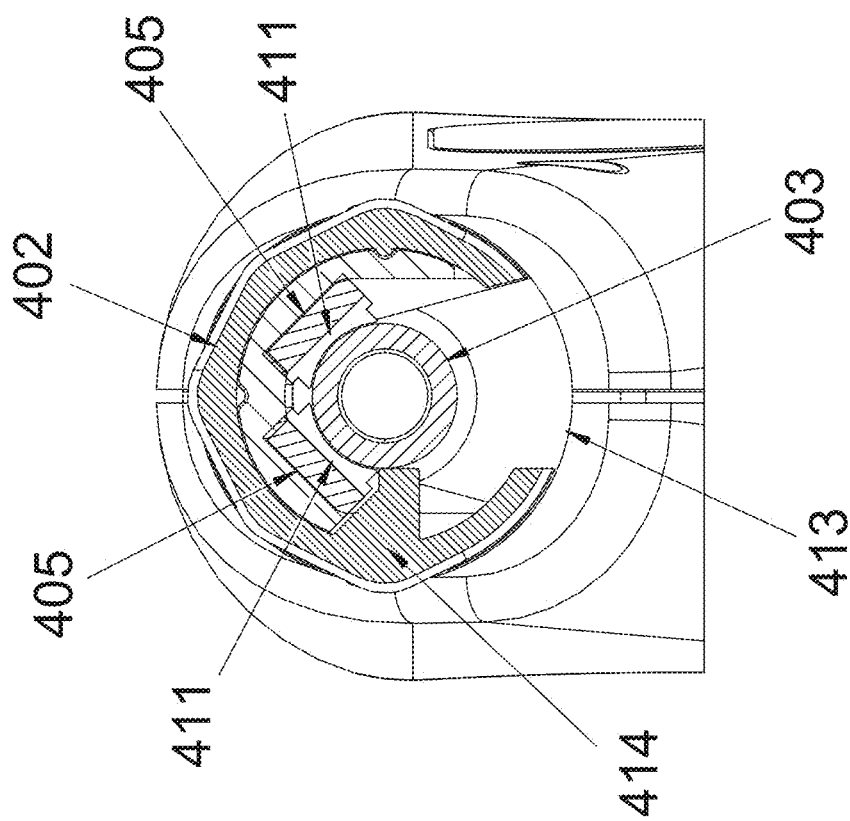
FIGURE (12b)
FIGURE (12a)

DEVICE AND METHOD FOR HEATING DENTAL COMPOSITE MATERIALS

RELATED APPLICATION DATA

The present application is a continuation-in-part of prior U.S. patent application Ser. No. 15/645,615 filed Jul. 10, 2017, incorporated herein by reference in its entirety.

FIELD OF THE INVENTION

The present invention relates to a dental applicator and a compule for applying dental material, more specifically to improved devices and methods for heating dental materials in compules.

BACKGROUND

With the advancement of light cured composite restorative dental materials, many dental materials have become much more viscous due to the higher levels of filler loading. Although the higher filler loading increases the strength and reduces the polymerization shrinkage of these materials, they have become very difficult to extrude from the compules they are packaged in. In addition, due to their clay-like handling characteristics they are also difficult to well adapt to the internal angles of the cavity preparation.

One method that assists in extruding highly viscous materials has been to heat the material prior to placement. Since most dental composite materials are packaged in molded plastic cartridges commonly referred to as compules, any heat from an external source needs to first overcome the thermal resistance or insulating nature of the plastics typically used to manufacture the compules. Prior art dental composite containers or compules are molded from plastic materials such as polyethylene, as well as polyvinyl chloride (PVC) and its derivatives.

One prior system includes a dispenser for heating and extruding dental material which includes drawbacks such as that the dispenser (holding and heating the compule) uses a dedicated microprocessor control circuit with an embedded thermocouple to control the current in the heater and in turn the temperature to which the composite material is heated. This arrangement adds significant cost to the manufacture of such a device. In addition, since the compule is molded from normal plastic material (e.g., polypropylene) which is a thermal insulator, the compule requires high power, high temperature and/or a lengthy heating time to overcome its thermal resistance. The composite material may then take a long time to reach the desired temperature.

SUMMARY

A heater assembly used in a dental material (e.g. composite) dispenser may be made of positive temperature coefficient (PTC) material such as barium titanate ceramic that may be self-regulating. A dental compule that holds dental material may be made from thermally conductive polymer or plastic, or other thermally conductive material, and/or may be made from electrically conductive plastic that is self-heating when an electric current is passed through the compule.

In one embodiment, a system heats and extrudes dental material from a compule or container. The system may include a compule or container made of a thermally conductive polymer forming at least a portion of the body of the compule, an orifice or extrusion opening positioned at one end of the compule, and an extrudable dental material held within the compule. A dispenser may include a receiving compartment removably receiving the compule, a movable plunger pressing on the compule to extrude the dental material held within the compule, and a heating unit made of a material having a positive temperature coefficient such that when electric current is applied to the heating unit its electrical resistance increases.

In one embodiment, a compule is generally cylindrical and is made from an electrically conductive polymer generating heat when electric current is applied to the polymer, two flat contact areas each disposed along one portion of the generally cylindrical compule, an orifice or opening positioned at one end of the compule, an inner chamber; and extrudable dental material held within the inner chamber. In an embodiment with a compule generating heat, a separate heater in a dispenser may not be needed.

In one embodiment a system includes a compule which includes an electrically conductive polymer generating heat when electric current is applied to the polymer, two flat contact areas each disposed along one portion of the compule, an orifice positioned at one end of the compule, and extrudable dental material held within the compule. The system may include a dispenser including a receiving compartment removably receiving the compule, a movable plunger for pressing on the compule to extrude the dental material held within the compule, and two electrical contacts.

In one embodiment the compule is made from a specially formulated electrically conductive resin polymer that itself has a PTC property. Such a material may heat to a predetermined temperature that remains constant so long as electrical current is applied.

BRIEF DESCRIPTION OF THE DRAWINGS

Features and advantages of embodiments of the present invention, as well as the invention itself, are more fully understood from the following description of various embodiments, when read together with the accompanying drawings.

FIGS. 12A and 12B show the details of PTC heaters, a compule and a holding flange according to an embodiment of the present invention.

Figure 1:
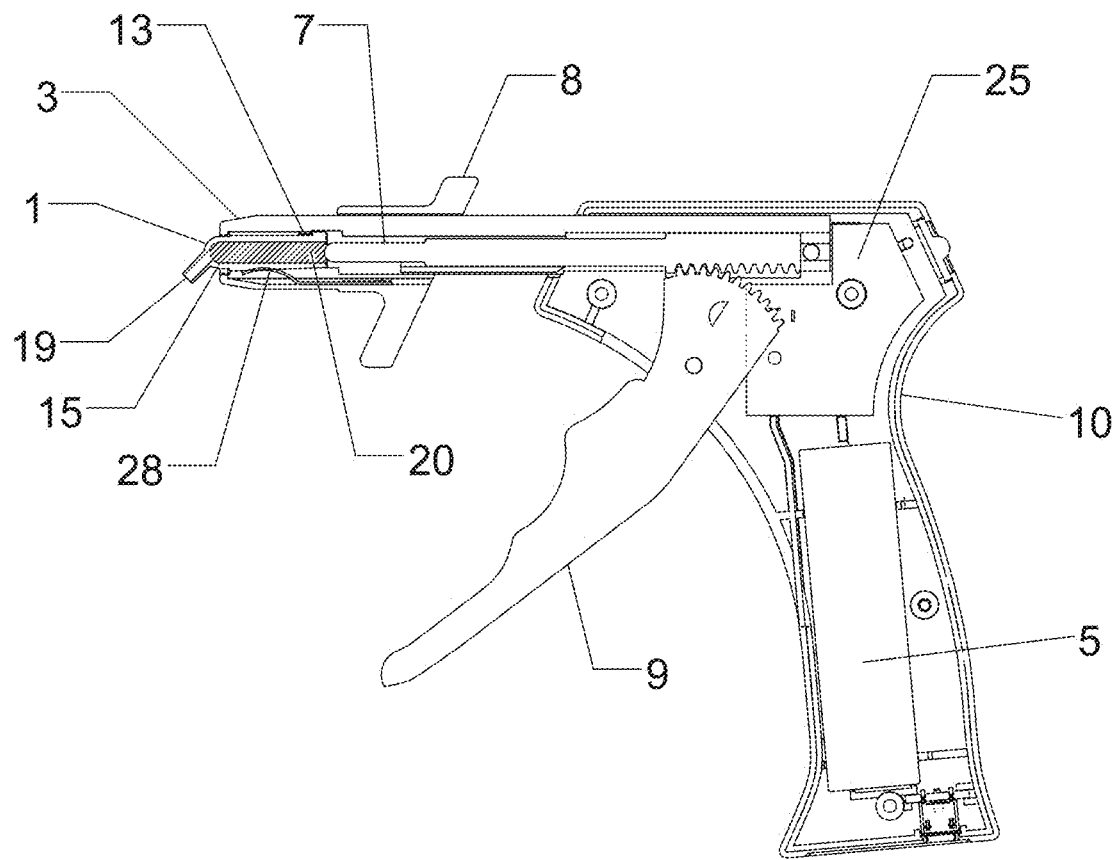
FIG. 1 shows in outline and cutaway form a dispenser that includes and may be used with various embodiments of the present invention, and a container or compule for extruding dental composite materials according to an embodiment of the invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that embodiments of the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Unless explicitly stated, the method embodiments described herein are not constrained to a particular order or sequence. Additionally, some of the described method embodiments or elements thereof may occur or be performed simultaneously, at the same point in time, or concurrently. Aspects from one embodiment may be combined with other embodiments.

One embodiment of the present invention is directed to a heater and compule combination that is designed to be simple, inexpensive and highly efficient. The heater may include or be made of a material having a positive temperature coefficient (PTC) such that when electric current is applied to the heating unit and heat is generated its electrical resistance increases thereby maintaining a selected temperature without external circuitry; such a material may be for example selected from a class of barium titanate ceramics. Such a heater may be a self-limiting heater.

Such a heater may be connected to a compule via a thermally conductive heat sink made from thermally conductive material, preferably metal, but which may be thermally conductive plastic that substantially fits, reproduces in reverse or mates with the shape of the compule. A compule may be made from for example conventional plastic or thermally conductive plastic.

A heater such as a PTC barium titanate heater can be molded with a semi-circular groove that may be shaped to accept the body of a circular composite compule which is in contact with the walls of the PTC heater material.

Other materials that can be used for self-limiting heaters may include those made from a mixture of polymer resins filled with conductive particles, or conductive plastics that can be self-limiting to be used as a self-limiting heater. For example, barium titanate ceramics may be obtained from DuPont, Research Triangle Park, N.C. Highly engineered polymer resin filled with conductive particles may be used for self-limiting heaters and may be obtained from Heatron, Leavenworth Kans.

When the resistance of the material making up the heater increases to a certain point current does not pass, stopping heating. The heater or heating unit may thereby maintain a selected temperature and may be self-regulating and not require a thermostat or micro-controller and may function without external circuitry.

A compule that is thermally and/or electrically conductive may be made of, for example, plastic such as a class of thermally conductive plastics, such as having base polymers such as polypropylene, polythalamide, polycarbonate, polyphenylene sulfide, and liquid crystal polymer. Such polymers typically would include carbon, graphite, steel or other metallic or electrically conductive fillers. Other materials can be used. While the thermal conductivity of non-heat-conductive plastics typically ranges from 0.10 to 0.50 W/mk, the thermal conductivity of thermally conductive plastics used with embodiments of the present invention may range from for example 1 W/mk to 100 W/mk. Other conductivities may be used.

In one embodiment the heater may be connected to a compule via, for example, a thermally conductive heat sink made from thermally conductive material, which may be metal, or, for example, thermally conductive plastic. A suitable heat sink may be made from, for example, copper, aluminum, brass or other metal, or from plastic such as a class of thermally conductive plastics, such as having base polymers such as polypropylene, polythalamide, polycarbonate, polyphenylene sulfide, and liquid crystal polymer. Such polymers typically would include carbon, graphite, steel or other metallic fillers. Other materials can be used. The heat sink may substantially fit the shape of all or a portion of the outside of the compule.

A compule in one embodiment may be made from a thermally conductive polymer or plastic such as for example COOLPOLY D5104, a thermally conductive plastic made from a base of polyphenylenesulfide (PPS), and a trademark product of Cool Polymers, Inc. USA, that efficiently transmits heat from the heat sink holding it to the composite material inside. Thermal conductivity may be, for example, in the range of between 1.0 w/mk and w/mk.

FIG. 1 shows in outline and cutaway form a dispenser 10 which includes and may be used with various embodiments of the present invention and a container or compule 1 for controllably extruding dental composite materials according to an embodiment of the invention. Some embodiments of FIG. 1 may be used with a compule having flattened portions along a side to enable adequate electrical connection. Some embodiments of FIG. 1 and other figures may be used with a conventionally shaped, or substantially cylindrically shaped compule, e.g. as shown in FIGS. 9-12. FIG. 1 shows aspects of multiple embodiments of the present invention, and not all components shown in FIG. 1 need be used with all embodiments described herein. For example, dispenser 10 of FIG. 1 may be used with a compule heated by a heater contained within dispenser 10 in which case components of compule 1 and dispenser 10 supplying current to compule 1 need not be used, and dispenser 10 may lack a heater and may be used with a self-heating compule made of electrically resistant material.

Figure 2:
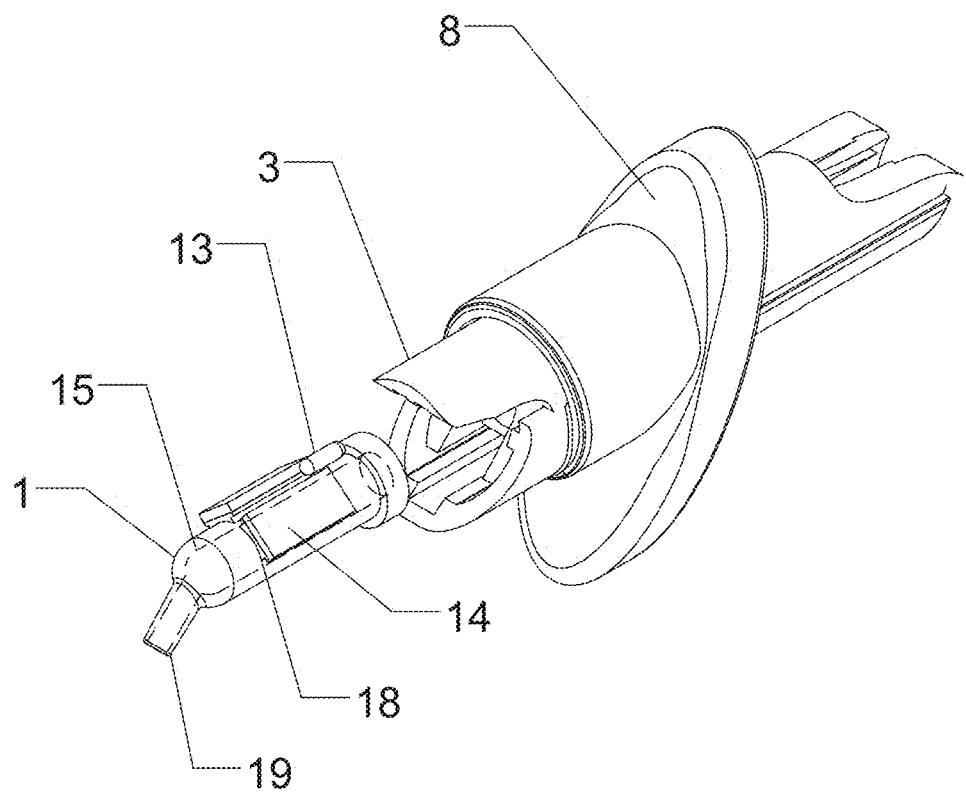
FIG. 2 shows a perspective view of a heater, compule and a portion of a dispenser according to embodiments of the present invention.
Figure 4A:
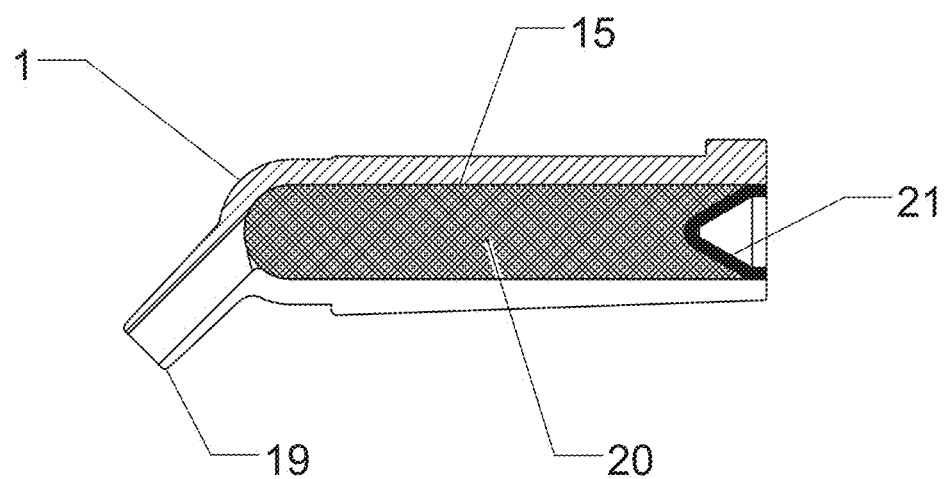
FIG. 4A depicts a cross-section of a molded container or compule according to an embodiment of the present invention.

FIG. 2 shows a perspective view of a heater and a portion of a dispenser according to embodiments of the present invention, with the compule removed from holding assembly 3. When in operation compule 1 is inserted in holding assembly 3. Compule 1 is typically cylindrical or barrel shaped with an inner chamber or cavity 15 holding dental composite material 20, as shown in FIG. 4A, and an orifice or nozzle 19 for dispensing material, but may deviate from a cylinder, e.g., by having one or more flat or substantially flat portions on a side, having one side be angled so that a spring or other structure may press on it, or by having any suitable size or shape other than a cylinder. Compule 1 may include one surface flat or angled to allow a spring to press against it to provide good contact against a heater element, electrical contacts, or a heat sink. Compule 1 may include a structure at the end opposite from orifice or nozzle 19 to facilitate the extrusion of said dental composite material using the dispenser; for example, a plunger cap 21 (shown more clearly in FIG. 4A) which may be moved axially in compule 1 by plunger 7 to force material out of orifice or nozzle 19. Compule 1 is typically removable and disposable but need not be.

Compule 1 may be contained or situated in a receiving compartment or holding assembly 3 of dispenser 10. Plunger 7 may be activated by lever arm or handle 9, which when pulled may cause plunger 7 to press on compule 1 to extrude dental composite material 20. Plunger 7 may include (e.g. at its forward end) a piston, or plunger 7 may act as a piston, and may be in coaxial alignment with the longitudinal axis of chamber or cavity 15 and in alignment with sealing plug or plunger cap 21 of compule 1 when compule 1 is inserted into dispenser 10. In one embodiment plunger 7 contacts and moves movable plunger cap 21 within the compule 1 as plunger 7 is advanced by manually squeezing the handle 9. Other methods and devices for applying force to a plunger, applying force to a compule, or extruding material from a compule, may be used, and other forms of a dispenser (e.g., other than a gun-shaped device) may be used.

A thermocouple 13 may act as a temperature monitoring sensor which together with, for example, a microprocessor control circuit or controller 25 acts a safety circuit back up in the event that heater 14 or compule 1 overheats. If compule 1 itself acts as a heater, thermocouple 13 may monitor compule 1 temperature and together with a microprocessor or control circuit, adjust compule 1 current to maintain a preset compule temperature. In one embodiment, controller 25 may sense the temperature of compule 1 and adjust, start or stop current flow to compule 1 to keep compule 1 temperature constant. The compule in this embodiment may be made from, for example, an electrically and/or thermally conductive polymer. In another embodiment, a controller need not be used, and compule 1 may self-regulate its temperature. The compule in this second embodiment may be made from, for example, an electrically conductive polymer having PTC characteristics. Controller or control circuit 25 may include for example a microprocessor that utilizes software or dedicated circuitry and feedback from a thermistor or thermometer or thermostat to control power to compule 1 during heating. Controller or control circuit 25 may interface with a control/display board (user interface) and may contain circuitry to properly charge power source 5. Controller may for example detect if an external power supply (e.g. via a USB or other connection) is connected, and if it is, engage in a battery charging operation, and if not, wait for a switch press or other command to start a compule heating process. Upon a switch press, current may be applied to compule 1 until a certain temperature, e.g., 155 degrees, is reached, at which time current is turned off until the sensed temperature of the compule falls to a certain level, when heating is resumed. A timeout may stop current to compule 1 after a certain amount of time regardless of compule temperature.

In one embodiment compule 1 may be self heating and be made from PTC material and thus not require a control circuit (e.g. control circuit 25 may be omitted). In one embodiment compule 1 may be self heating but may require an external thermistor and control circuit 25. In a further embodiment compule 1 may not be self heating but may be made from thermally conductive plastic, and thus may require control circuit 25 and heating unit 14, but not structures described herein to deliver current to compule 1. Typically, compule 1 that requires a control circuit is made from electrically conductive plastic and compule 1 that is self heating and does not require a control circuit is made from a specially formulated electrically conductive plastic that exhibits sufficient PTC characteristics. In some embodiments, increased crystallinity of the polymer as well as the crystallinity of the conductive filler (e.g., carbon black) may create an increased PTC effect which may be used in a self regulating compule not requiring a controller. In one embodiment, low crystalline materials may have less PTC effect, and thus external controller 25 may be used with compules including such materials.

Dispenser 10 may include a power source 5 such as a battery (e.g. a lithium ion battery or another suitable battery), connectable to a heating element 14, although power may be supplied externally, e.g. via a cord. Power source 5 may provide, for example, in one embodiment 3.9 Volts DC at 0.8-1.5 Amps, power to heating unit 14 and/or compule 1 itself, in the event compule 1 itself acts as the heater. Other voltages and current ranges may be used. Heating unit 14 may be, for example, a PTC ceramic heater, or another suitable heater, and may be part of holding assembly 3.

Figure 3:
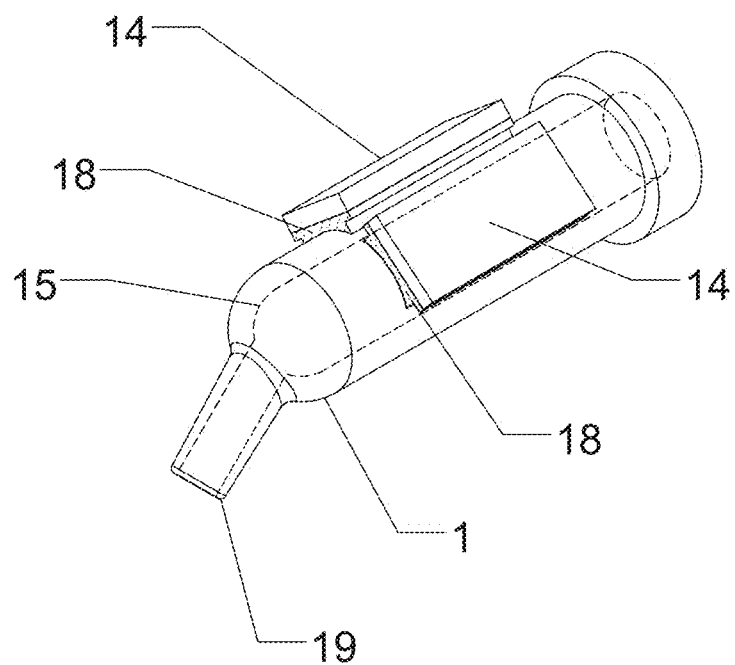
FIG. 3 depicts heaters and heat sinks pressed against a compule according to an embodiment of the invention.

A cutaway portion of a distal end of dispenser 10, with disposable container or compule, 1, is shown in FIG. 2 and FIG. 3. In FIG. 2, receiving compartment 3 is partially disassembled, as compule 1, heater 14, and heat sink 18 are shown removed from and outside of a receiving compartment or holding assembly 3. Compule 1 can be inserted in and removed from receiving compartment or holding assembly 3.

Heating unit 14 may be connected or bonded to a heat sink 18 which in turn may make physical contact with compule 1 such that between 10% and 100% of the compule surface is in contact with one or more heat sinks 18. In one embodiment heating unit 14 may be rectangular and relatively flat and may be bonded to a curved metallic heat sink 18, which may be flat on the side that is bonded to heater 14 and curved on the other side, shaped to fit the cylindrical surface of compule 1. Such an arrangement may create a good thermal contact between heater 14 and compule 1. More than one heating unit 14 and/or heat sink 18 may be used. Heating unit 14 may be fabricated in such a manner that the shape of the heating unit 14 itself makes good contact with compule, 1 and eliminates the need for heat sink 18 (e.g., heating unit 14 curved to fit a barrel or cylinder).

Heating unit 14 may be made of one or more PTC materials and may be formed of a class of ceramics (such as barium titanate or lead titanate composites) or from a polymer type PTC heater. Such materials have a highly nonlinear thermal response, so that they become extremely resistive above a composition-dependent threshold temperature. This behavior causes the material, and heating unit 14, to act as its own thermostat. Its electrical resistance increases as current flows through the material which stabilizes to a preset temperature at equilibrium. Simply stated, current passes when it is cool, and does not when it is hot.

Compule 1 may be molded from a plastic that has greatly improved thermal, and possibly electrical, conductivity, such as synthetic thermoplastics, polypropylene, liquid crystalline, polyamide and polyphenylene sulfide. The heat conductivity of these plastics ranges from 1 W/mk to over 100 W/mk. These materials have 5 to 500 times the thermal conductivity of conventional plastics. Some of these materials are manufactured by Cool Polymers Inc, North Kingstown R.I. 02852.

Figure 7:
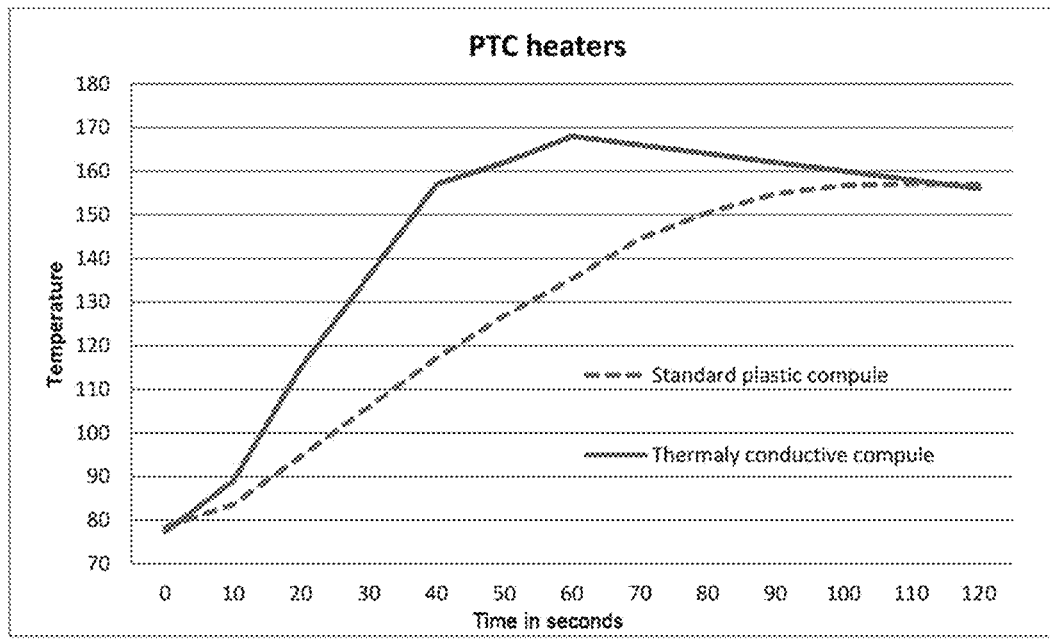
FIG. 7 is a graph depicting heating times of compules including an example compule according to an embodiment of the present invention.
Figure 8:
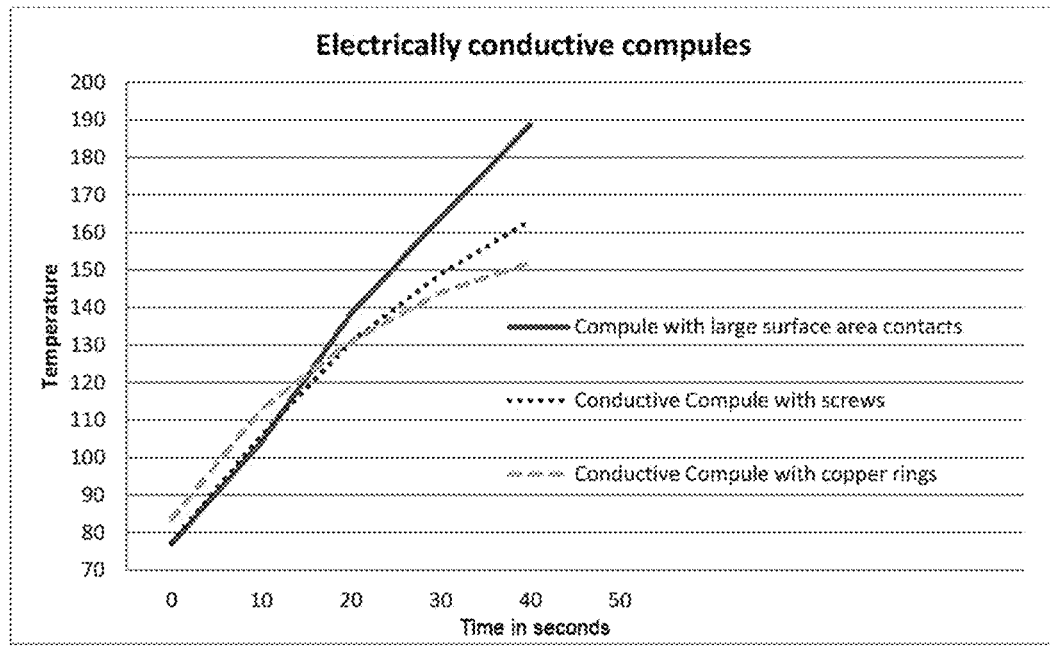
FIG. 8 is a graph depicting heating times of compules including an example compule according to an embodiment of the present invention.

The effect of a compule with a large contact area and a large electrical contact placed under pressure creates a heater out of the compule itself. Since the internal walls of the compule are in intimate contact with the composite or other material inside, the material heats very quickly compared to a compule made of standard plastic. This effect is well demonstrated by comparing the composite temperature in FIG. 7, which show that it takes approximately 90 seconds (1.5 minutes) to reach 155° F. in a standard compule, whereas the electrically conductive compule whose performance is shown in FIG. 8 heats to 155° F. in about 25 seconds, more than 3.5 times faster. FIG. 8 also shows the response times for electrically conductive compules drilled and assembled with screws as electrical contacts and another version using copper rings molded into the compule and used as electrical contacts. During dental restorative procedures, this time difference is extremely important. The need for fast compule heating is made critical when a patient is anesthetized and compules are changed during treatment due to additional material required for larger restorations or the need to change shades to achieve an accurate shade match.

FIG. 2 shows a perspective view of heater 14, heat sink 18 and thermocouple 13, all of which may fit into holding assembly 3 of FIG. 1. Slider 8 may be used whether compule 1 provides heat or is externally heated to ensure that compule 1 makes good electrical contact (e.g. low contact resistance and high current flow) with an electrical supply; and/or good heating contact with a heat sink or heater for good heat transfer. This may be done, for example, in conjunction with leaf spring 28.

FIG. 3 depicts heaters 14 and heat sinks 18 contacting or pressed against compule 1 according to an embodiment of the invention. In one embodiment two heat sinks are positioned so that compule 1 can be removed from receiving compartment or holding assembly 3. Other numbers of and arrangements of heat sinks and/or heaters may be used.

FIG. 4A depicts a cross-section of molded container or compule 1 made from one or more of a material which heats when electric current is applied, a plastic that has improved thermal conductivity, a conventional plastic, and other materials, according to embodiments of the invention. Compule 1 may hold dental composite material 20 in chamber or cavity 15. FIG. 4A also shows the compule nozzle 19 and a plunger cap 21. The plunger 7 shown in FIG. 1 may be activated by the dispensing mechanism and may push the heated material 20 out of the nozzle 19.

Dental material 20 is typically preheated prior to dispensing. Examples of dental material 20 include restorative materials (commonly referred to as filling materials), etching agents, bleaching compositions, dental cements, impression materials and particularly normal and photocurable dental restorative materials.

One embodiment may eliminate the need for an external heater located, for example, in a dispenser used to heat dental material in a container or compule. In one embodiment, a container or compule may be made of an electrically and/or thermally conductive polymer which generates heat when an electric current is applied to the polymer. In such an embodiment, the dispenser holding the compule may not need its own heater, eliminating structure and possibly some or all circuitry from the dispenser. Since the compule is now itself the heating element, heating may be much more efficient, and the material may be heated significantly faster. The compule may include surfaces or structures allowing for a high amount of electric current to be applied. For example, the compule may be generally tube or cylinder shaped with an inner chamber holding dental material and may also include two or more flat or substantially flat contact areas each disposed along one portion of the compule, against which corresponding electrical contacts may touch or be pressed. The container or compule may include at one end an orifice to extrude dental material, and at the other end a moveable plug or seal, which when pressed by a dispenser plunger or other structure causes material to be extruded. The dispenser used with an embodiment of this compule may lack a heater, but may include a power source (e.g. battery, wired external power source, etc.) applying power via two or more electrical contacts. The compule may be removably placed in a receiving compartment of the dispenser. The dispenser may include a movable plunger pressing on the compule to extrude the dental material held within the compule when, for example a handle or trigger is pressed.

An embodiment of the dispenser may include a control such as a slider or handle which, when activated, presses the compule against the electrical contacts to ensure a good electrical connection and ensure a large amount of current can be transferred to the compule. The slider may slide over a leaf spring disposed in the receiving compartment to cause the leaf spring to press on the compule, to press the compule against the flat contacts when the slider presses on the leaf spring. Alternately the slider may cause the leaf spring to press electrical contacts against the compule. The slider may be movable from a position not pressing on the leaf spring to a position pressing on the leaf spring (e.g. towards the distal end of the dispenser).

In one embodiment a compule may be made of material having high thermal conductivity and electrical resistivity. Having the compule be made of material having high thermal conductivity may aid in heat transfer to dental material when electrically conductive material in the compule heats the compule itself. In one embodiment electrically conductive material also has high heat conductance. For example, a plastic having for example a thermal conductivity in the range of between 1.0 w/mk (watts per meter-kelvin) and 500 w/mk and an electrical resistivity in the range 0.01 and 10,000 ohm-cm may be used. Other parameters may be used. One suitable plastic material s COOLPOLY D5104, a thermally conductive plastic made from a base of polyphenylenesulfide (PPS), and a trademark product of Cool Polymers, Inc. USA for an electrically conductive material, which may also be thermally conductive. A compule formed from a thermally conductive material having a thermal conductivity in the range from 1.0 w/mk to 500 w/mk may cause a dental composite restorative material stored in the compule to be heated up two or three times faster than it would under conditions in prior art compules.

Using a conventional purely cylindrical compule design may not allow for low electrical contact resistance that permits high current flow and subsequent heating of the composite material. Unlike metallic materials, electrically conductive plastic typically has lower electrical resistance and the simple placement of small electrical contacts as one might do with metal materials may not provide significant current flow in conductive plastic materials. To permit the effective heating of this type of container or compule, in one embodiment several conditions are created (other embodiments may not use all conditions, and other characteristics may be used).

Figure 4B:
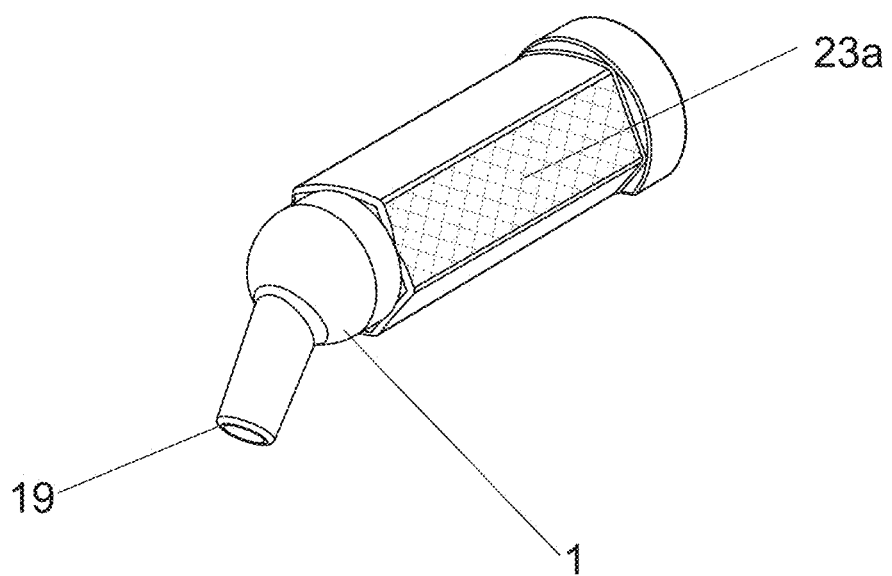
FIG. 4B depicts a container or compule according to an embodiment of the present invention.
Figure 4C:
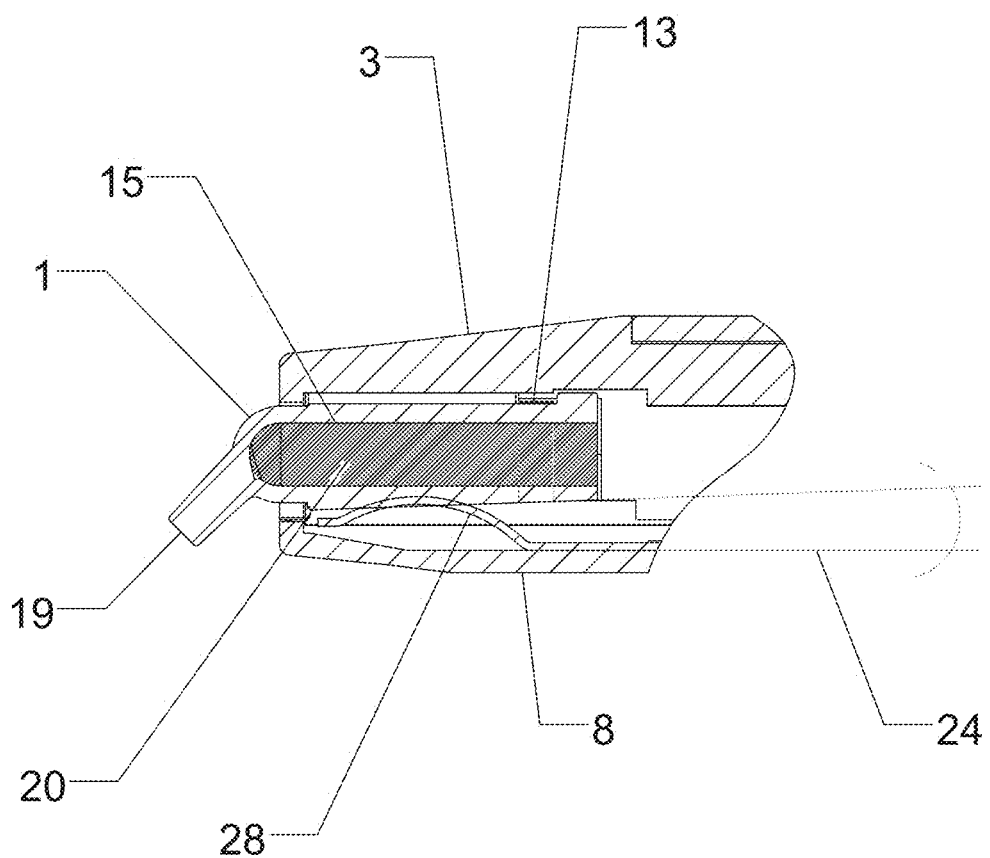
FIG. 4C depicts a container or compule according to an embodiment of the present invention.
Figure 4D:
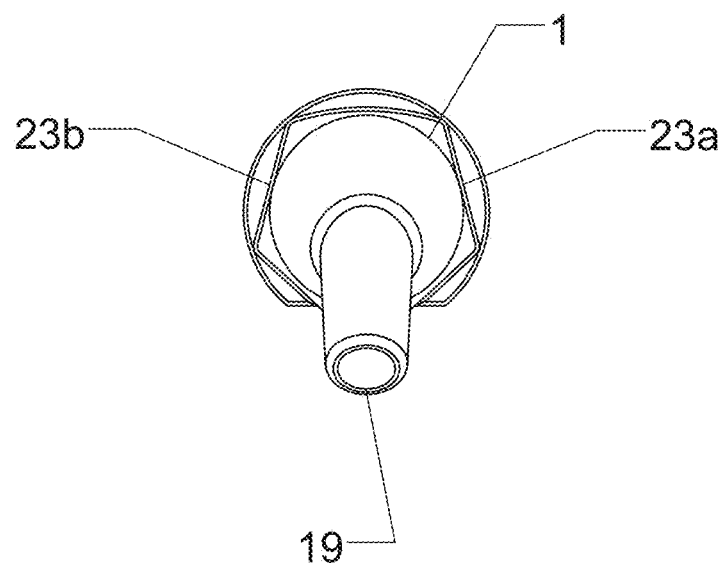
FIG. 4D depicts a container or compule according to an embodiment of the present invention.

FIG. 4B depicts a container or compule according to an embodiment of the present invention. Referring to FIG. 4B and FIG. 4C, compule or container 1 may have two or more large flat electrical contact areas relative to its size such as 23a and 23b, for example, flat areas are shown in a hatched pattern. Contacts 16a and 16b, shown in FIG. 5 and FIG. 6, may provide current from a power source to compule 1 and may be, for example, gold plated. It is desirable that a large area of electrical contact come in very intimate relation with compule 1 so that high current can quickly flow through the wall structure of compule 1. It is desirable that the contacts be placed onto the compule with reasonably high force to achieve low contact resistance and a high initial current of, in one embodiment, at least 0.5 Amps. Compule 1 may include on one portion an angled bottom as shown in FIG. 4C to allow a spring to press against it to, for example, provide good contact against a heater, electrical contacts, or a heat sink. The angled bottom may allow for a progressive force to be applied via slider 8.

In one embodiment the internal volume of compule 1 is approximately (e.g., +/−30%) 0.36 cubic inches, but other volumes may be used. Compule 1 may be, for example, approximately 0.8 inches long excluding the orifice tube. The wall thickness of compule 1 may be for example approximately 0.5 inches. Other dimensions may be used.

Figure 5:
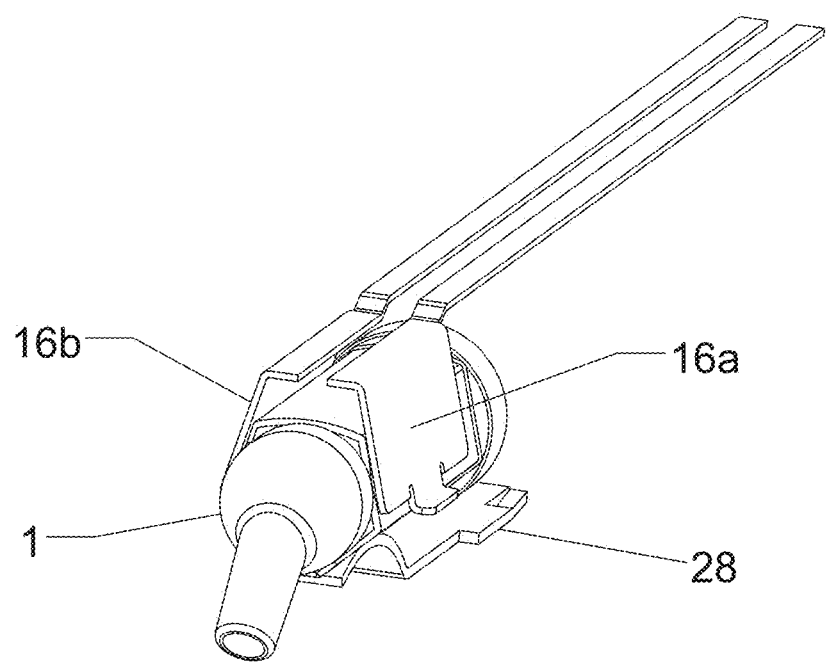
FIG. 5 shows portions of the dispenser of FIG. 1 in combination with a compule according to embodiments of the invention
Figure 6:
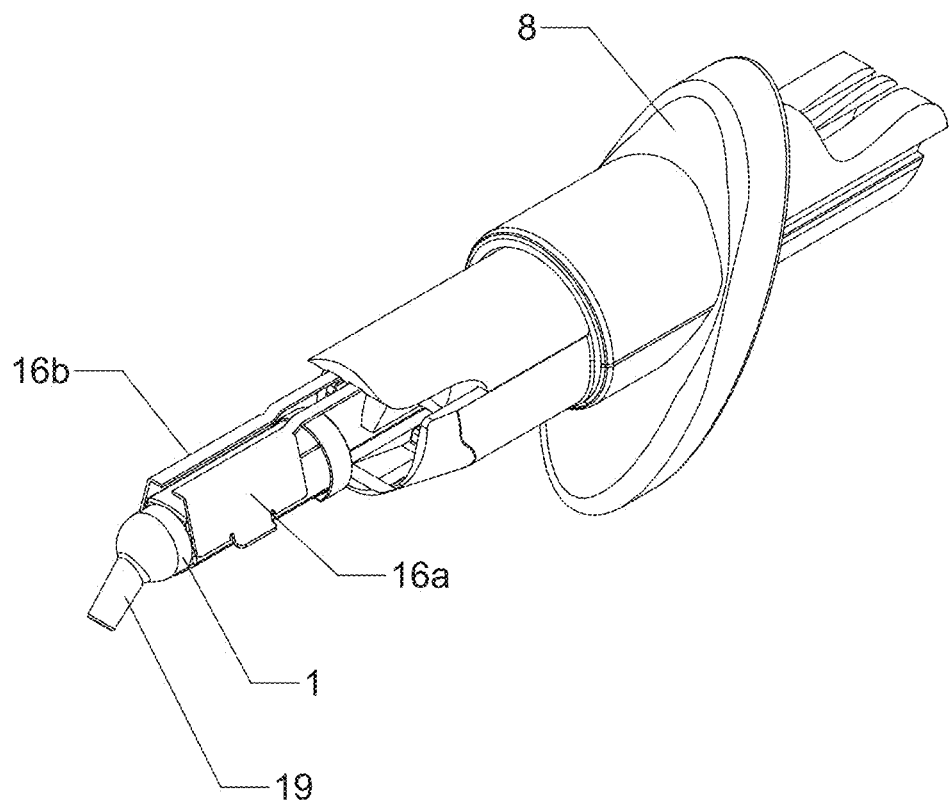
FIG. 6 shows portions of the dispenser of FIG. 1 in combination with a compule according to embodiments of the invention.

FIG. 4C shows the critical angle 24 between the bottom of compule 1 and a horizontal reference which may provide a ramping function such that as the slider 8 rides over leaf spring 28 it forces compule 1 tightly against electrical contacts 16a and 16b, as shown in FIG. 5 and FIG. 6, to provide a low resistance contact and high current flow. As slider 8 containing or connected to spring 28 is moved forward to secure compule 1, spring 28 rides on an angled bottom of compule 1 and progressively increases the force on compule 1. In one embodiment the angle should be no less than 2 degrees and can be 20 degrees or higher. Other angles are possible. The angle may be "critical" as it may in part determine the force the spring contact or leaf spring 28 places on compule 1. In one embodiment the force produced by spring 28 is in the range of 1-6 lbs (0.45 Kg to 2.3 kg); other forces are possible. Electrical contacts 16a and 16b may be located on one side of compule 1, the other side being generally curved and/or free of electrical contacts, to allow compule 1 to be removably inserted in compartment or holding assembly 3.

Leaf spring 28 may alternately press electrical contacts against a compule, and other methods of pressing a compule and contacts together may be used. Electrical contacts 16a and 16b may be connected to power source 5 such as a battery, although power may be supplied externally, e.g. via a cord. Typically, the ratio of total compule contact area of contact areas 23a and 23b to total cylindrical surface area of compule 1 is approximately 27%; other ratios may be used. It is desirable that this be greater than 15% in order to provide the high current flow needed to heat compule 1 in 30 seconds or less. In one embodiment, each of contact areas 23a and 23b may be for example a rectangle of approximately (e.g., +−10%) 0.635 inches by approximately (e.g., +−10%) 0.157 inches and the contacts 16a and 16b include for example a rectangular area (possibly with cutouts and tabs) of approximately (e.g., +−10%) 0.22 inches by approximately (e.g., +−10%) 0.54 inches. Other dimensions may be used.

To operate the dispenser 10 in one embodiment, compule 1 is inserted in holding assembly 3, and slider 8 is moved from an "open" position to a "closed" position towards the distal end of dispenser 10, pressing compule 1 and contacts 16a and 16b together. Leaf spring 28 may be located in the receiving compartment on an opposite side of compule 1 from the side including the flat contact areas 23.

FIG. 4C, FIG. 5 and FIG. 6 show portions of the dispenser of FIG. 1 and the embodiments of FIG. 4C, FIG. 5 and FIG. 6 are meant to be used with an embodiment of the dispenser of FIG. 1. In FIG. 6, the compule and electrical connections are shown partially disassembled from the main device, to show internal components.

Contact areas 23a and 23b may be positioned not completely opposite to each other on the generally cylindrical portion of the container or compule, rather located at a less than a 180 degree angle to each other (when measured around the circumference of the container or compule), such that when leaf spring 28 or another structure presses the compule in one direction, both contact areas 23a and 23b of compule 1 are pressed towards and against both contacts 16a and 16b. Thus, within or relative to the receiving compartment, contacts 16a and 16b or the area between contacts 16a and 16b may be positioned opposite on compule 1 to leaf spring 28. Other arrangements or positions of electrical contacts may be used.

Compule 1 is typically cylindrical or barrel shaped with an inner chamber holding dental material and an orifice for dispensing material, but may deviate from a cylinder, e.g., by having one or more flat portions on a side, or by having a shape other than a cylinder.

FIG. 5 and FIG. 6 show a set of electrical contacts 16a and 16b having a large contact area which are positioned, when compule 1 is inserted into receiving compartment or holding assembly 3, on either side of compule 1. FIG. 5 shows leaf spring 28 that applies pressure against the compule 1 to minimize the contact resistance and permit high instantaneous current flow through electrically conductive compule 1. When slider 8 (FIG. 6) is moved forward by the operator, it in turn forces the leaf spring 28 against the compule 1 and in turn against the electrical contacts 16a and 16b. This ensures that good contact is made to allow for high current flow and subsequent fast compule heating.

The effect of a compule with a large contact area and a large electrical contact placed under pressure may create a heater out of the compule itself. Since the internal walls of the compule are in intimate contact with the composite or other material inside, the material heats very quickly compared to a compule made of standard plastic. This effect is well demonstrated by comparing the composite temperature in FIG. 7, which shows that it takes 90 seconds (1.5 minutes) to reach 155° F. in a standard container or compule (dotted line), and a thermally but not electrically conductive compule (solid line) heats to 155° F. in about 38 seconds in one example, whereas an electrically conductive compule according to one embodiment as shown in FIG. 8 heats, for example, to 155° F. in about 25 seconds, almost 3.6 times faster. During dental restorative procedures, this time difference may be important. The need for fast compule heating is particularly critical when a patient is anesthetized and compules are changed during treatment due to additional material required for larger restorations or the need to change shades to achieve an accurate shade match.

Embodiments shown in FIGS. 9-12 may include some benefits, features or components of FIGS. 1-6, and vice versa. In FIGS. 9-12, a dispenser and compule combination are shown where a standard, off the shelf, generally cylindrical compule (e.g. with typically no flat portions on its circumference may be used with a heater such as a PTC plastic heater or a barium titanate ceramic heater. For example, a standard compule may be used where the compule is made from or includes as at least part of its body a normal polymer material such as polypropylene, acrylonitrile butadiene styrene (ABS), polycarbonate, or polyethylene. One embodiment includes advantages such that it may heat all commercially available compules in the dental market, and also a thermally conductive compule as stated. However, other compules, such as those shown in FIGS. 1-6, may be used. Other suitable materials may be used.

A heater or heater assembly can be molded with a semi-circular opening 413 which may be shaped and/or sized to accept the body of a circular or substantially circular (in cross-section) composite compule which is in contact with the walls of the PTC heater material. A conventionally shaped compule—e.g. a substantially cylindrical compule—which is made from (or where at least a portion of the body of the compule is made from) heat-transmitting plastics or thermally conductive polymer (e.g. a thermally conductive polymer or plastic as discussed elsewhere herein) or other thermally conductive materials may transfer heat faster than a conventional compule made from conventional plastics, which do not transmit heat well. A compule used with embodiments of FIGS. 9-12 may be substantially cylindrical in that the ends of the compule may not be cylindrical, e.g. may include curved portions, a dispenser tip, etc.

Advantages of using a thermally-conductive polymer may include faster heating time. Advantages of using a PTC heater may include the elimination of the need for external heat and/or current controlling circuitry. In some embodiments a dispenser may achieve fast heating of specially designed compules made from thermally conductive plastic and also be able to be used with standard off the shelf compules, both compules having the same substantially cylindrical shape which is a dental industry standard. Other shapes may be used.

Figure 9:
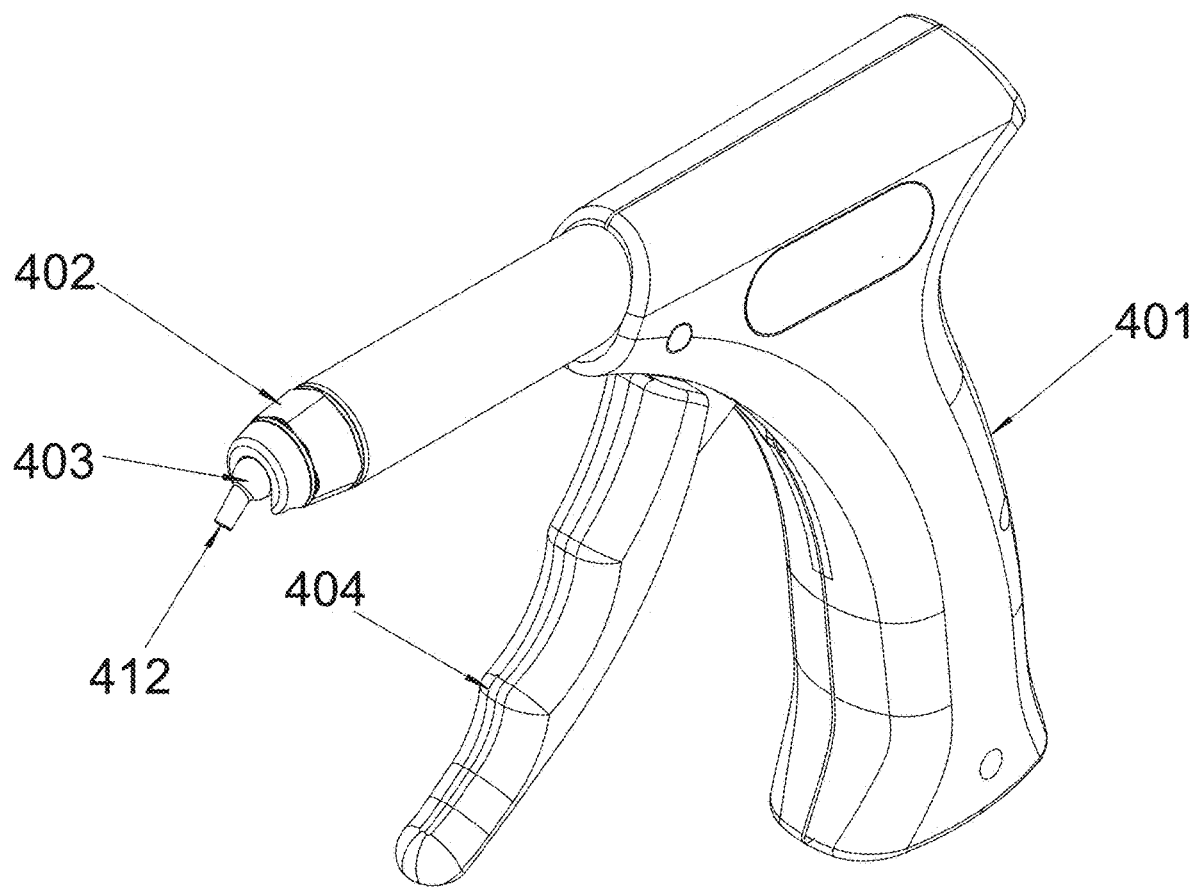
FIG. 9 shows dispenser gun with a rotating locking member or sleeve that can press a compule against PTC heaters with curved mating surfaces according to an embodiment of the present invention.
Figure 10:
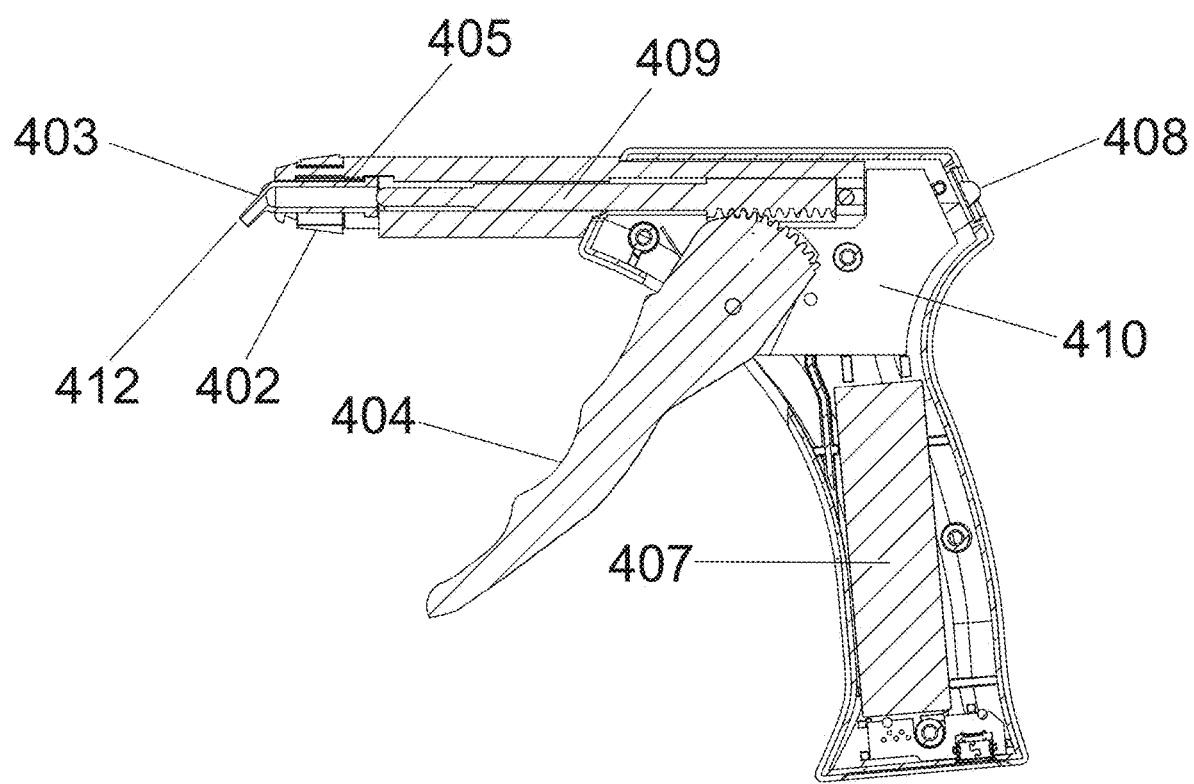
FIG. 10 depicts an outline cutaway view that shows the inner details of a dispenser gun with cutaways of a mechanically-loaded holding member, compule, and plunger according to an embodiment of the present invention.
Figure 11:
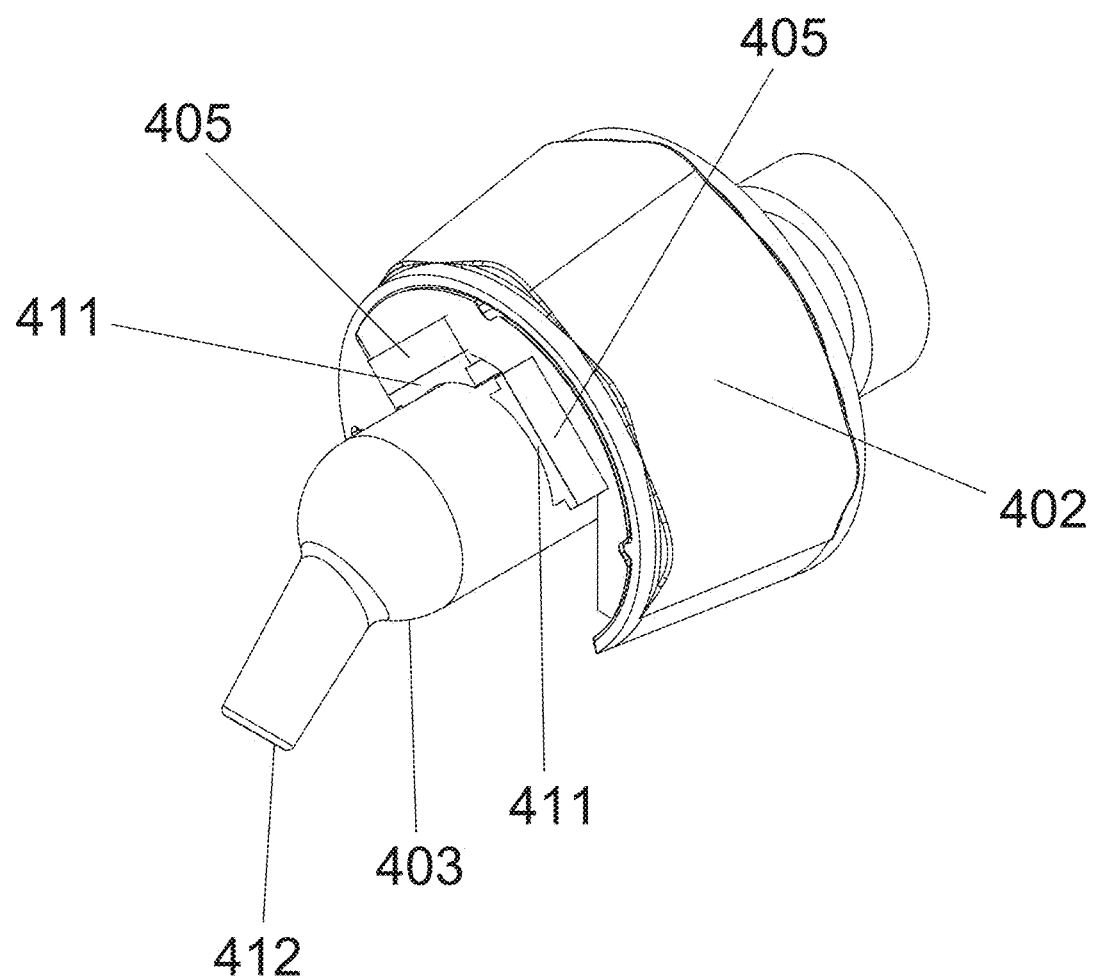
FIG. 11 shows details of PTC heaters in contact with a compule made from plastic or thermally conductive plastic according to an embodiment of the present invention.

FIG. 9 shows a perspective view of one embodiment of a heating dispenser 401, which is used to heat compule 403 (only a portion of which is visible). Referring to FIGS. 9, 10 and 11, heating elements 405 (only a portion of which are visible) may be PTC heaters. Heating elements 405 may include material having a positive temperature coefficient such that when electric current is applied its electrical resistance increases Compule 403 may include a moveable sealing plug at one disposed, as described elsewhere herein, and may include other features as described elsewhere herein.

Dispenser 401 may include a receiving or holding compartment removably receiving compule 403. The receiving compartment may be formed in part by or may include a locking or retaining member, sleeve or other device such as a rotating locking member or ring 402 which may removably capture, retain or hold compule 403 and press it against PTC heaters 405 (pressing against heaters 405 may include pressing against heat sinks disposed between heaters 405 and compule 403), which is connected to, attached to or in communication with heat sinks 411 (FIGS. 11 and 12) to insure good thermal heat transfer from heaters 405 to compule 403. Heat sinks 411 may be part of, be disposed, or from part of a receiving compartment. Once compule 403 reaches proper temperature, trigger 404 may be pulled back by the operator (e.g. a dental professional) so that movable plunger 409 (FIG. 10) moves forward and presses on or against the composite material inside compule 403 which will extrude or force out warmed material through orifice 412 located at one end of compule 403. Composite material used in the system of FIG. 9 and held within compule 403 may be for example extrudable dental material 20 discussed above.

FIG. 10 shows a cross section view of heating dispenser 401 according to embodiments of the present invention. Compule 403 is heated by PTC heating unit or heater 405 attached to heat sink 411. Heat sink 411 is preferably made from a metal or metallic material with good thermal conductivity. When trigger 404 is pulled back, it moves plunger 409 forward to extrude the warmed composite material out of the compule 403 via orifice 412. Other components, such as a controller, power supply, etc. may be for example those described with respect to FIGS. 1-6. In some embodiments a dispenser using a PTC heater does not need a microcontroller, temperature sensing element and/or specialized software. Rather, only switch 408 is used to turn the PTC heater on and off, and to connect the PTC heater to battery 407, which to supplies electric power. In this embodiment, a circuit board 410 may be used simply to support an on/off switch 408 and connection terminal for battery 407.

FIG. 11 shows a detailed perspective view of the thermal connection between PTC heaters 405 and other elements, according to embodiments of the present invention, with a shape that permits close physical and thermal contact between the PTC heater and the cylindrical shape of compule 403. In this example, the compule is cylindrical or substantially cylindrical in shape; in one embodiment at least a portion, or a portion, or the compule is cylindrical or substantially cylindrical. The ends of the compule may deviate from being cylindrical e.g. a front-end having orifice 412. In this configuration, each heat sink 411 has one flat side or flat surface bonded to or otherwise in communication with PTC heater 405 and the other side curved to mate or communicate with the cylindrical shape of compule 403. Each heat sink 411 may include a flat side disposed against the heating unit 405 and a curved side disposed against compule 403. In an embodiment where compule 403 has, for example, flat sides, heat sinks 411 may have one flat side attached to PTC heater 405 and the other side mating with compule 403 may be flat as well.

In some embodiments, one or more (e.g. two) heaters 405 may be used, with flat portions mating with heat sinks: thus, it may be considered that a heating unit used with the system has two or more separate heaters. A "heating unit" may also be considered to include heat sinks. Other numbers of heaters and heat sinks may be used. One or more heat sinks 411 may connect with or be in communication with both heater 405 and compule 403. For example, one heat sink 411 each may connect to each heater 405. Heaters 405 and heat sinks 411 may be arranged to connect with or contact less than half of the circumference of compule 403 for example to allow compule 403 to fall away or be removed when a retaining member such as rotating locking member 402 is rotated to permit an opening 413 to be created or moved into position. For example, when compule 403 is inserted in the receiving compartment heat sinks 411 (which may be one heat sink) partially surround compule 403, extending around no more than half the circumference of compule 403

FIG. 12A shows a cross-section view of an embodiment of compule 403 with heat sinks 411, PTC heaters 405 and rotating locking member 402. Compule 403 may be inserted via insertion opening 413. With compule 403 in place, rotating locking ring member 402 is turned counterclockwise which both moves opening 413 to be over a portion of dispenser 401 which blocks compule 403 from escaping, and puts pressure from the locking ring onto the surface of the compule 403.

FIG. 12B shows a cross section view of an embodiment of locking ring 402 rotated to be in the closed position with the insertion opening 413 eliminated or no longer presented, as being over another portion which holds compule 403 in place. In this locked position, the compule 403 is held in place by extension 414 of locking ring member 402. Simultaneously, locking ring member 402 via extension 414 may put pressure on the compule 403 against heat sinks 411 which are attached to PTC heaters 405. It is in this position that the heated composite material within compule 403 can easily be expressed through orifice 412 by the operator pulling back on trigger 404 which moves plunger 409 forward. Once the material is expressed from the compule, the locking member 402 may be rotated for example clockwise. This movement rotates opening 413 shown in FIG. 12A to a position to allow now empty compule 403 to drop out. Locking member or ring 402, possibly via extension 414, may apply pressure against compule 403, pressing it against heat sinks 411 or heaters 405, which may provide for good thermal contact between compule 403 and the heating assembly (e.g. heater(s) possibly combined with heat sink(s)), which may increase the speed at which the composite material inside compule 403 is heated.

Figure 13:
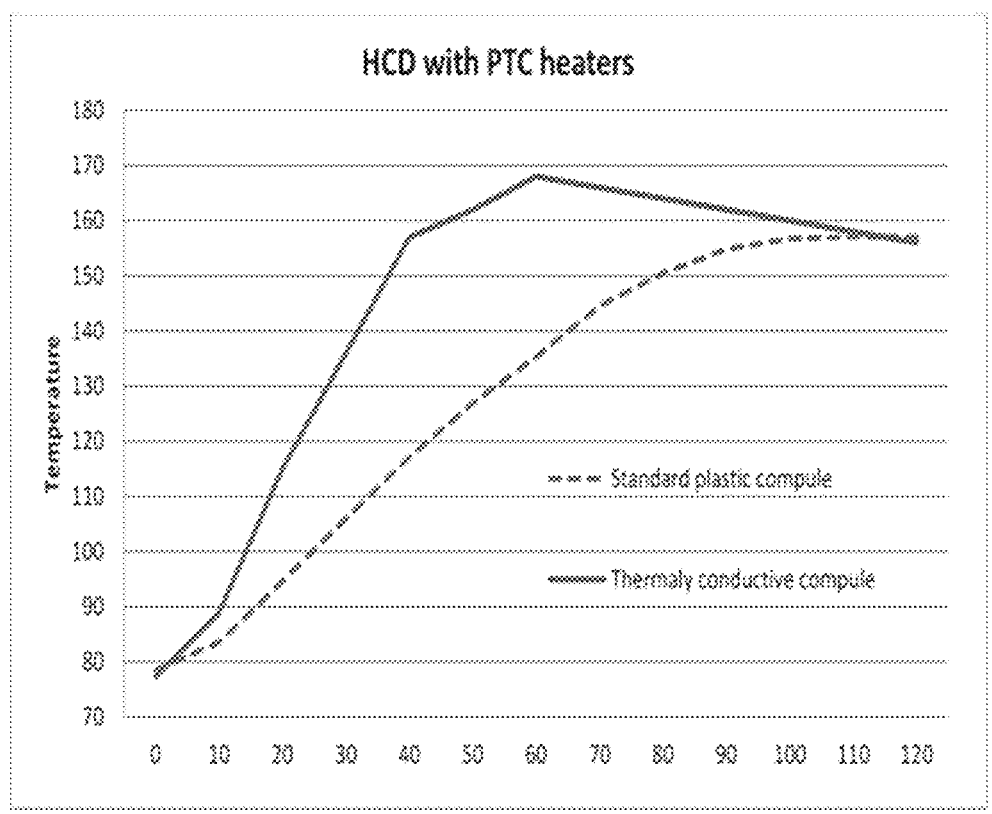
FIG. 13 show shows the rate of heating for a standard plastic compule and a thermally conductive compule according to embodiments of the present invention.

FIG. 13 is a graph which demonstrates the advantage in heating composite contained in a thermally conductive compule compared with a standard plastic compule using PTC heaters, according to one embodiment. In one example it takes 90 seconds (1.5 minutes) to reach 155° F. in a standard compule (dotted line), while a thermally but not electrically conductive compule (solid line) heats to 155° F. in about 38 seconds. Other values of course may be achieved.

In one embodiment compule 1 or in some embodiments compule 403 may be made from a highly engineered, PTC electrically conductive filled resin polymer. This material may have increased electrical resistance with temperature such that a predetermined temperature is maintained without the use of external thermostats or electronic control circuits. Such a compule, and a dispenser, is described above, but controller 25 may be omitted. One possible advantage of making a compule from a PTC electrically conductive filled resin polymer may be an ability to self regulate to a predetermined temperature. In its simplest form this would consist of such a PTC compule connected directly to battery or any power source without the need for additional control or thermal management circuitry. Further, as discussed, a heater which is part of a dispenser may be made of PTC materials discussed herein.

One example of a PTC thermoplastic material is described in US patent application number 2008/0039575, entitled, "Thermal conductive polymeric PTC compositions", by Franciscus Petrus Maria Merex, 2008, incorporated by reference herein in its entirety. This patent describes a wide range of plastic resins that are combined with a specific filler loading of graphite or carbon black. These materials have PTC characteristics such that when an electric current is applied, they will heat to a pre-determined temperature and maintain this constant temperature indefinitely.

Materials having a PTC composition may be made from a semi-crystalline thermoplastic polymer having a degree of crystallinity of at least 5%, carbon black, and graphite having a carbon content of at least 99% and a particle size of at least 10 microns. Other PTC materials may be used.

A list of possible thermoplastic polymers may include for example polyethylene, polypropylene, polyvinyl acetate, polycaprolactone polyesters, syndiotactic polystyrene (sPS), polyamides, poly-tetra-fluorethylene, polybutylene-terephthalate, polyphenylene-sulfide, high-density polyethylene, linear low-density polyethylene, low-density polyethylene, mid-density polyethylene, polyisobutylene, poly(vinylidene chloride), poly(vinylidene fluoride), polyacrylonitrile, polybutadiene, polyethylene-terephthalate, poly(8-aminocaprylic acid), polyvinyl alcohol), ethylene-based co- and terpolymers, maleic anhydride modified polyethylene, glycidyl methacrylate modified polyethylene, maleic acid anhydride modified polypropylene, glycidyl methacrylate modified polypropylene, or blends, mixtures or combinations of one or more of these polymers. Other suitable polymers may be used.

Such materials may include additives, such as for example fillers, antioxidants, lubricants, flame retardants nucleating agents, coupling agents, ultraviolet absorbers, ultraviolet stabilizers, pigments, dyes, agents, plasticizers, processing aids, viscosity control agents, tackifiers, anti-blocking agents, surfactants, extender oils, metal deactivators, voltage stabilizers, boosters, catalysts, smoke suppressants, or combinations thereof. Other suitable additives may be used.

Other examples of PTC materials and polymer composite plastics are referenced in the article, "PTC Effect and Structure of Polymer Composite based on Polyethylene/Polymethylene Blend Filled with Dispersed Iron". Y. P. Mamunya, Y. V. Muzychenko, et al. published in Polymer Engineering and Science 2007.

Mamunya et al. describes example materials which may be used in compute 1, for example high density polyethylene (PE) HMJ 6382 M, Russian standard GOST 16336-77, with density 0.94 g/cm3 and melt flow index (MFI) equal to 1.6 g/10 min, in the form of powder, polyoxymethylene (POM), Russian standard TU 6-05-1543-72, with density 1.40 g/cm3 and MFI ¼ 10.9 g/10 min, in the form of powder, and iron powder R-10 (Fe), Russian standard GOST 13610-79, with average size of particles 3.5 mm and shape of the particles close to spherical. These materials may be used to produce combinations of PE-Fe, POM-Fe, and a blend PE/POM-Fe with the volume content of the components specified.

Various dental composite materials may be used with embodiments of the present invention, such as Bis-GMA and other dimethacrylate monomers (e.g. TEGMA, UDMA, HDDMA) and filler materials such as silica, quartz or ceramic. In many applications, a photoinitiator is also added. There is typically a direct correlation between composite flow and temperature such that the higher the temperature the greater the flow for all composite materials. Other materials may be used.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention. Various embodiments have been presented. Each of these embodiments may of course include features from other embodiments presented, and embodiments not specifically described may include various features described herein.

The invention claimed is:

1. A system configured for heating and extruding dental material from a compule, the system comprising:
   a compule being, at at least a portion, substantially cylindrical, and comprising:
      a polymer forming at least a portion of the body of the compule;
      an orifice positioned at one end of the compule; and
      extrudable dental material held within the compule; and
   a dispenser comprising:
      a receiving compartment removably receiving the compule;
      a movable plunger for pressing on the compule to extrude the dental material held within the compule;
      a heating unit comprising a material having a positive temperature coefficient such that when electric current is applied to the heating unit the electrical resistance of the heating unit increases;
      a heat sink disposed in the receiving compartment connected to the heating unit, the heat sink comprising a flat side disposed against the heating unit and a curved side disposed against the compule, substantially fitting the shape of at least a portion of the compule, to create a thermal contact between the heating unit and the compule; and
      a battery providing electric current to the heating unit.

2. The system of claim 1 wherein the heating unit comprises one or more heaters.

3. The system of claim 1 wherein the heating unit comprises two heat sinks arranged to contact an area of less than half the circumference of the compule.

4. The system of claim 1 wherein the material of which the heating unit is comprised of barium titanate ceramic.

5. The system of claim 1 wherein the compule comprises a polymer selected from the group consisting of polypropylene, acrylonitrile butadiene styrene (ABS), polycarbonate, and polyethylene; the polymer forming at least a portion of the body of the compule.

6. The system of claim 1 wherein the compule comprises a thermally conductive polymer forming at least a portion of the body of the compule.

7. The system of claim 1 comprising a sleeve operable to press the compule against the heating unit.

8. A system configured for heating and extruding material from a compule, the system comprising:
   a compule made from a thermally conductive substance forming at least a portion of the body of the compule, the body of the compule having a cylindrical portion and no flat portion on the circumference of the compule, the compule comprising:
      an opening; and
      extrudable material held within the compule; and
   a dispenser comprising:
      a compartment removably receiving the compule;
      a plunger for pressing on the compule to extrude the material held within the compule;
      at least one heater comprising a material having a positive temperature coefficient such that when electric current is applied to the heater the electrical resistance of the heater increases;
      a heat sink disposed in the compartment connected to the heater, the heat sink comprising a flat side disposed against the heater and a curved side disposed against the compule, substantially fitting the shape of at least a portion of the compule, to create a thermal contact between the heater and the compule; and
      a battery providing electric current to the heater.

9. The system of claim 8 wherein the heat sink comprises metallic material.

10. The system of claim 8 wherein the dispenser comprises two heaters.

11. The system of claim 8 wherein the dispenser comprises two heat sinks arranged to contact an area of less than half the circumference of the compule.

12. The system of claim 8 wherein the heater comprises barium titanate ceramic.

13. The system of claim 8 wherein the compule comprises a moveable sealing plug at an end opposite the end at which the opening is positioned.

14. The system of claim 8 comprising a retaining member operable to press the compule against the heater.

* * * * *